US006645435B2

(12) United States Patent
Dawson et al.

(10) Patent No.: US 6,645,435 B2
(45) Date of Patent: Nov. 11, 2003

(54) APPARATUS AND METHOD FOR PROVIDING A CONTINUOUSLY SANITIZED CONTACT SURFACE

(76) Inventors: Paul Wesley Dawson, 1133 Pinecreek Rd. S., Callander, Ontario (CA), P0H 1H0; Scott Hough Shanks, 3486 Talbot Trail R.R. 1, Wheatley Ontario (CA), N0P 2P0

( * ) Notice: Subject to any disclaimer, the term of this patent is extended or adjusted under 35 U.S.C. 154(b) by 175 days.

(21) Appl. No.: 09/972,387

(22) Filed: Oct. 9, 2001

(65) Prior Publication Data

US 2002/0041824 A1 Apr. 11, 2002

Related U.S. Application Data
(60) Provisional application No. 60/239,111, filed on Oct. 11, 2000, and provisional application No. 60/284,947, filed on Apr. 13, 2001.

(51) Int. Cl.$^7$ .............................. A61L 2/18; B08B 3/04
(52) U.S. Cl. ................ 422/110; 422/37; 422/292; 422/300; 422/28; 422/105; 134/104.1; 134/115 R; 4/662
(58) Field of Search .................. 422/37, 105, 292, 422/300, 28, 110; 134/115 R, 104.1; 4/662; 239/53, 57

(56) References Cited

U.S. PATENT DOCUMENTS 4,329,815 A * 5/1982 Secrest ......................... 47/80
6,289,557 B1   9/2001 Manson et al.

FOREIGN PATENT DOCUMENTS

| CA | 2122335 | 11/1992 |
| CA | 2011809 | 5/1993 |
| CA | 2296152 | 6/2000 |
| EP | 0931497 A2 * | 7/1999 |

* cited by examiner

*Primary Examiner*—Robert J. Warden, Sr.
*Assistant Examiner*—Sean E. Conley
(74) *Attorney, Agent, or Firm*—Lynn Cassan

(57) ABSTRACT

An apparatus and method for providing a contact surface which is continuously sanitized with a sanitizing fluid. A reservoir contains the sanitizing fluid. A contact material has a porous contact surface in fluid communication with the reservoir. A moisture control and fluid distribution system determines the moisture level of the porous surface and, upon determining that the moisture level thereof has reached a predetermined level, causes a flow of the sanitizing fluid from the reservoir to the contact material. The contact material comprises a durable, porous outer layer configured for evenly distributing the sanitizing fluid to the contact surface and a backing layer bonded to the outer layer to provide a seal there between.

19 Claims, 2 Drawing Sheets

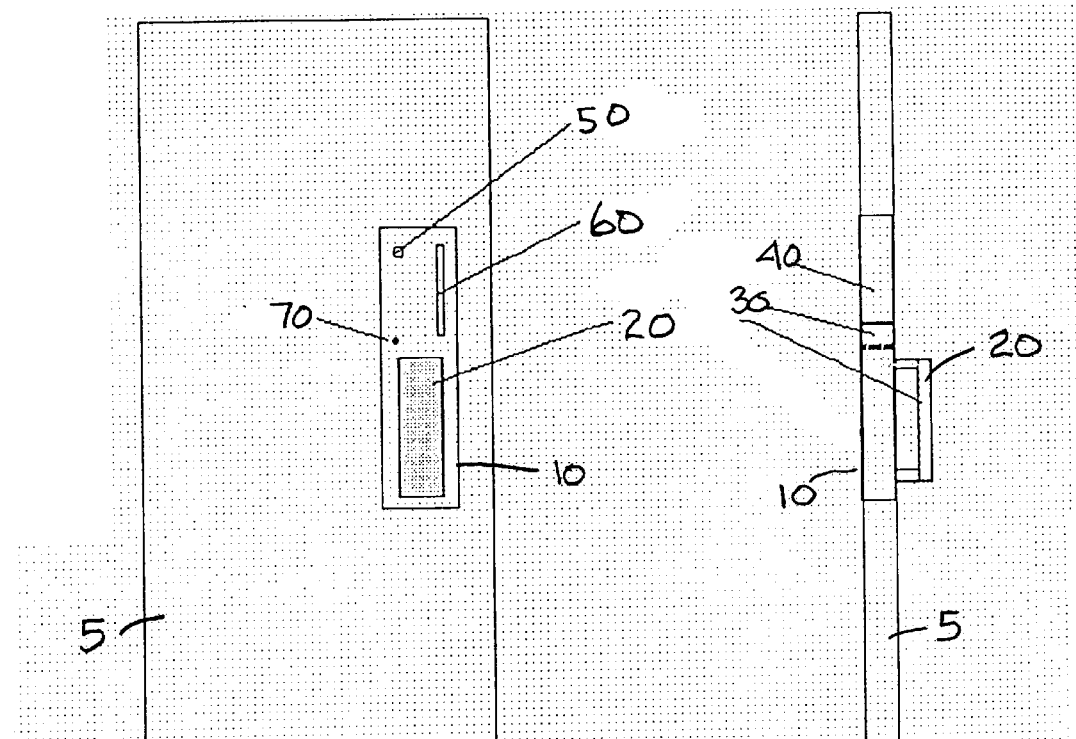
FIG. 1
FIG. 2
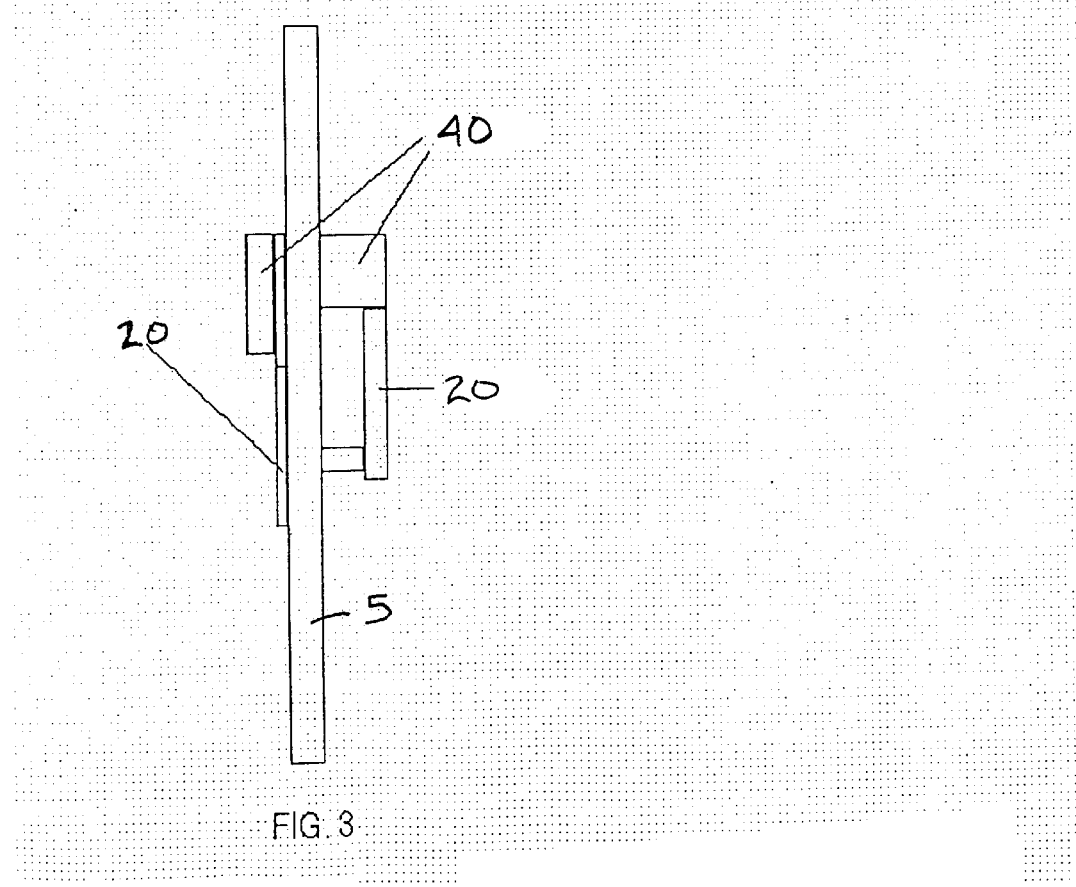
FIG. 3

US 6,645,435 B2

APPARATUS AND METHOD FOR PROVIDING A CONTINUOUSLY SANITIZED CONTACT SURFACE

This application claims benefit of Provisional Applications Ser. No. 60/239,111 filed Oct. 11, 2000, and Ser. No. 60/284,947 filed Apr. 13, 2001.

FIELD OF INVENTION

This invention relates to an apparatus and method for rendering sanitary (i.e. germ-free) a contact surface, such as a door handle, on a continuous basis.

BACKGROUND OF THE INVENTION

For safety and sanitary reasons, hospitals, laboratories and commercial establishments are increasingly in need of means for maintaining sanitary certain facilities within their premises such as kitchen and washroom areas. Typically, a form of soap and hand drying method is provided within such facilities but it is known that a percentage of the population does not adhere to effective hand washing following consumption of food and/or using washroom facilities, or following the handling of chemicals, reagents, etc. within a hospital or laboratory, and this results in the transfer of germs, bacteria and/or viruses to surface areas which come into contact with individuals. Moreover, the provision of a soap and hand drying facility is relatively expensive because it requires labour to maintain and may also involve energy costs and wastage costs.

A lesser known means of protecting contact surfaces against the spread of germs is disclosed in published Canadian Patent Application No. 2,296,152 in the name of Lane Kendall Herman which appears to have been filed Jan. 12, 2000 and published on Jun. 20, 2000. That application discloses a sanitation system for dispensing an alcohol-based sanitiser over a surface (such as a door handle) by using touch controlled external or internal nozzles to spray the handle after it has been used and sensors to sense when the handle is being touched. The apparatus and method therein disclosed deposits (but does not retain) a sanitiser onto a contact surface and, thus, requires that the sanitiser be a highly volatile chemical (i.e. alcohol) in order that it evaporate quickly so as to leave the handle relatively dry soon after it is treated. Such fluids are not desirable for general use due to their relatively high flammable nature. The apparatus and method therein disclosed also undesirably uses a touch flow control system, for controlling the flow of the volatile fluid based on touch, and such flow systems are not desirable because they typically provide uneven coverage of the fluid due to the non-porous nature of the surface areas typically contemplated and the low viscosity of a nozzle-sprayed alcohol-based fluid. Additionally, a touch-activated flow control system is subject to cause flooding of the handle, and dripping of fluid onto the floor, if used repetitively.

Therefore, it is desirable to provide an improved and cost-effective means for providing a sanitising, safe material to a surface contact area. It is further desirable to provide means for evenly controlling and distributing such a sanitiser.

SUMMARY OF THE INVENTION

In accordance with the invention there is provided an apparatus and method for providing a contact surface which is continuously sanitized with a sanitizing fluid. A reservoir contains the sanitizing fluid. A contact material having a porous contact surface is in fluid communication with the reservoir. A moisture control and fluid distribution system determines the moisture level of the porous surface and, upon determining that the moisture level thereof has reached a predetermined level, causes a flow of the sanitizing fluid from the reservoir to the contact material. The contact material comprises a durable, porous outer layer configured for evenly distributing the sanitizing fluid, which is relatively non-flammable and may be chlorine-based, to the contact surface and a backing layer bonded to the outer layer to provide a seal there between.

In use, the contact material may be formed as desired to cover any surface area, such as a door handle, to provide a continuously sanitized surface therefore. Optionally, the contact material may be integrated within an object to provide such object with a continuously sanitized surface therefore. The moisture control and fluid distribution system preferably comprises a fluid flow control circuit and a flow controller for controlling the flow of fluid from the reservoir to the contact material in response to an output from the fluid control circuit. At least one transducer is preferably installed at the contact surface to produce a signal correlated to the moisture level at the contact surface for input to the fluid flow control circuit.

DESCRIPTION OF THE DRAWINGS

The present invention is described in detail below with reference to the following drawings in which like reference numerals refer throughout to like elements:

FIG. 1 is a front view of a door equipped with a sanitary contact surface apparatus in accordance with the present invention, the contact surface covering an extended longitudinal door handle;

FIG. 2 is a side view of the door of FIG. 1 showing a cross-section view of the sanitary contact surface apparatus installed therein;

FIG. 3 is a side view of a door equipped with an alternate embodiment of the sanitory contact surface apparatus of the present invention, wherein a flush-mounted contact surface is provided on the left side of the door and an extended contacted surface, covering a longitudinal door handle, is provide on the right side of the door;

DETAILED DESCRIPTION OF PREFERRED EMBODIMENTS

Figure 4:
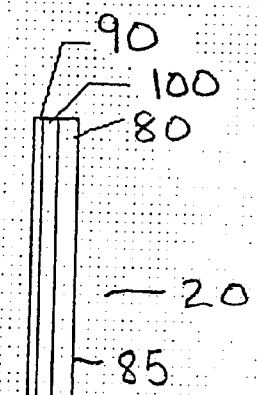
FIG. 4 is a cross-sectional view of a preferred contact material used for the sanitary contact surface apparatus of the invention, the contact material having a backing layer and a porous outer layer which distributes a sanitizing fluid across the contact surface and provides a durable contact surface.

FIG. 1 of the drawings illustrates a front view of a door 5 equipped with a sanitary contact surface apparatus in accordance with the present invention, wherein the sanitized contact surface covers an outwardly extended longitudinal door handle, and FIG. 2 illustrates a side view of this embodiment. In this embodiment a sanitizing fluid reservoir

40, a moisture control and fluid distribution system (see components 120, 121, 30 and 130 of FIG. 7) and a contact material 20 are produced as a single unit and inlaid into the door 5 to provide an installation which is integral to the door and does not significantly alter the appearance of the door. In the embodiment illustrated by FIGS. 1 and 2 an outwardly extended handle is covered with a contact material 20. If desired, for an alternate embodiment, a push pad flush with the door surface could instead be used and covered with a like contact material. The contact material 20 comprises a durable, porous surface which distributes, over the surface, a non-flammable sanitizing fluid delivered from the reservoir 40 to the body of the contact material 20. The delivery and flow of the sanitizing fluid is controlled by a fluid flow control circuit (see component 120 of FIG. 7) and a transducer (see probe 121 of FIG. 7) which detects the moisture level of the surface 85 of the contact material 20.

The sanitizing fluid selected for the preferred embodiment is a chlorine-based chemical solution as this provides a relatively non-flammable fluid (as compared to an alcohol-based solution) and also provides the required germicide function. However, It is to be understood that the term "sanitizing fluid" used herein is not intended to be limited to any particular type of chemical solution or fluid and the scope and meaning of this term includes any suitable fluid which acts as a germicide. Optionally, a scent additive may be included in the fluid in order that the sanitizing fluid may function also as an air freshener.

With reference to FIG. 1, a reservoir sight level window 60 is preferably included to enable the user to monitor the fluid level of the reservoir 40 and a fluid fill aperture 50 is provided to fill the reservoir with sanitizing fluid. A battery charge indicator 70 is also preferably included to indicate the charge remaining on a battery which powers the moisture transducer (sensor) and fluid flow control circuit of the moisture control and fluid distribution system.

FIG. 3 illustrates an alternate embodiment of the sanitary contact surface apparatus of the present invention in which the fluid reservoir 40 is mounted externally to the door 5, rather than integrally within the door 5 and, thus, the appearance of the door 5 is changed by the installation of the apparatus. As shown, for this illustrated embodiment a flush-mounted contact surface is provided on the left side of the door 5 and an extended contacted surface, in the form of a longitudinal door handle, is provide on the right side of the door 5.

FIG. 4 shows a cross-sectional view of the contact material 20 of the apparatus of FIGS. 1–3. A backing layer 90 is bonded to an outer porous layer 80 and seals the material so that sanitizing fluid within the body of the contact material 20 does not leak or come into contact with the surface over which the contact material 20 is installed (for example, the metal or wooden surface of a door handle). The backing layer 90 may be comprised of a foam rubber or neoprene, for example, or any other suitable material. The outer layer 80 is made of a durable, porous material chosen such that it will evenly distribute the sanitizing fluid across the contact surface 85 provided by the contact material. The outer layer 80 is, in the preferred embodiment, comprised of a nylon which serves as a tough fabric layer. However, for an alternate embodiment any other porous material which is suitable to render the surface 85 sufficiently durable to withstand both the wear of usage and continuous saturation by the sanitizing fluid could be used. An inner absorbent layer 100, such as a sponge layer, is optionally included to provide an inner material for retaining and holding the sanitizing fluid close to the surface 85. Further, It is to be noted that a backing layer sealed to the porous contact surface may not be desired if the surface of the object over which it is installed is such that it will not be damaged by contact with the sanitizing fluid. For such an alternate embodiment, the contact material may consist solely of a fabric (e.g. nylon) which is suitable for distributing the fluid throughout itself using capillary action.

Figure 6:
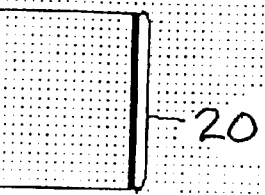
FIG. 6 is a cross-sectional view of the sleeve of FIG. 5 taken at section C—C; and, FIG. 7 is a schematic block diagram illustrating the combination of components of a sanitary contact surface apparatus in accordance with the invention.
Figure 5:
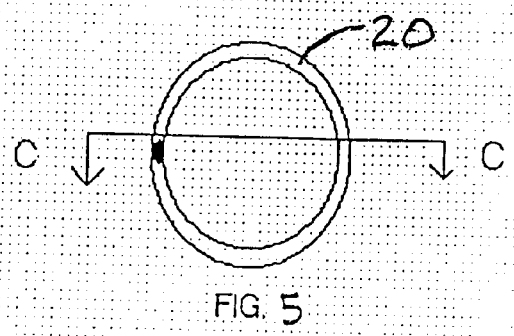
FIG. 5 shows the contact material of FIG. 4 formed as sleeve which can be slid over a door knob or handle.

The contact material 20 may be manufactured in many shapes or as sleeves (see FIGS. 5 and 6). The outer covering 80 may be a heat shrinkable fabric (such as aircraft covering dacron) which can be mass produced and fitted tightly to handles, knobs or any other contact surface of various shapes. The material 20 may be provided as a removable outer cover over a door or window handle, or other contact surface, or may be integrally incorporated into a handle or other contact surface at the time of manufacture of such items. Optionally, the contact material 20 may be formed with inner distribution channels to transfer the sanitizing fluid to different areas of the surface 85 thereof.

The sanitizing fluid at the surface 85 of the contact material 20 is constantly removed through evaporation and items coming into contact with the surface such as persons' hands. Therefore, it is necessary that the apparatus be able to provide a fresh supply of the sanitizing fluid to the contact material 20 on a continuing and controlled basis.

Figure 7:
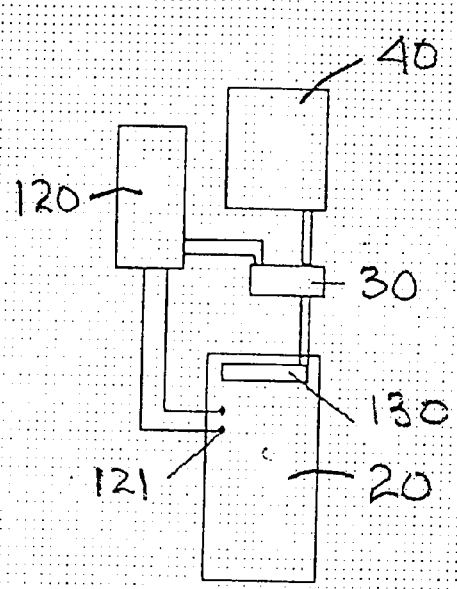

FIG. 7 illustrates, in block diagram form, the interaction of the components of the sanitary contact surface apparatus of the present invention. The sanitizing fluid reservoir 40 holds a supply of the sanitizing fluid. The flow of the sanitizing fluid from the reservoir 40 to the contact material 20 and contact surface 85 is controlled by a flow controller 30, being a pump or solenoid valve. A suitable fluid flow control circuit (with a power supply) 120 controls the flow controller 30 on the basis of control signals it receives from one or more transducers (i.e. moisture sensors) 121 at the surface 85 of the contact material 20. When the contact surface 85 reaches a predetermined level of dryness the circuitry 120 is triggered to activate the flow controller 30 and cause it to allow more sanitizing fluid to flow through a manifold 130 to the contact material 20.

Moisture/fluid flow control circuits are well-known and readily available in the marketplace and no claim is made herein to the fluid flow control circuit itself. For example, for information concerning suitable circuits, the reader is referred to the publication entitled *The Encyclopedia of Electronic Circuits,* FIG. 56-3, "Automatic Plant Waterer", and Section 56, "Moisture and Rain detectors", 1985, Tab Books Inc., Blue Ridge Summit, Pa. 17214. For the sanitary contact surface apparatus of the present invention, a suitable moisture/fluid flow control circuit with moisture transducer (s) is provided to maintain a predetermined (selected) moisture level at the surface 85 of the contact material 20. Such circuits typically operate on the principal that as the contact surface dries, the resistance between two spaced apart probes positioned on the surface will increase. The probes may be provided externally to the contact material 20 or, instead, may be formed as conductive fibers woven into the contact material.

It is to be understood that the specific types, configurations and components of the contact material, reservoir, moisture control and fluid distribution system described herein with reference to the illustrated embodiments are not intended to limit the invention; for example, the invention is not intended to be limited to any specific configuration for the contact area, for which various alternative embodiments may be determined by one skilled in the art based upon the teachings herein and the particular application. Further, it is to be recognized that the moisture control and fluid distribution system disclosed herein is not limited to any particular type of system and alternative systems utilizing mechanical moisture valves and/or optical control sensing and/or other sensing and control means might instead be selected and/or the viscosity of the sanitizing fluid itself to achieve flow control. Further the apparatus claimed herein is not limited for use on any particular type of object or in any particular installation.

In accordance with a different aspect of the invention a continuously sanitized contact surface is provided by a solidified sanitizing material configured to form a coating layer over a surface which, through the wear of usage, is depleted over time. A preferred embodiment of this aspect of the invention provides continuous sanitization to a contact surface by means of the coating layer only.

The present invention may be embodied in other specific forms without departing from its spirit or essential characteristics. The described embodiments are to be considered in all respects only as illustrative, and not restrictive. The scope of the invention, is therefore, defined by the appended claims, and not by the foregoing description. All variations and equivalents coming within the meaning of the appended claims are intended to be embraced within the scope of the present invention.

What is claimed is:

1. An apparatus for providing a contact surface which is continuously sanitized with a sanitizing fluid, said apparatus comprising:
    (a) a reservoir for containing said sanitizing fluid;
    (b) a contact material having a porous contact surface in fluid communication with said reservoir; and,
    (c) a moisture control and fluid distribution system for controlling the moisture level of said contact surface whereby a flow of said sanitizing fluid from said reservoir to said contact material is produced when said moisture level has reached a predetermined level.

2. An apparatus according to claim 1 wherein said sanitizing fluid is a chlorine-based, relatively non-flammable fluid.

3. An apparatus according to claim 2 wherein said contact material comprises a durable, porous outer layer configured for evenly distributing said sanitizing fluid to said contact surface and a backing layer bonded to said outer layer to provide a seal there between.

4. An apparatus according to claim 3 wherein said contact material is configured for covering the surface area of an object.

5. An apparatus according to claim 4 wherein said moisture control and fluid distribution system comprises a fluid flow control circuit, a flow controller for controlling the flow of fluid from said reservoir to said contact material in response to an output from said fluid flow control circuit and at least one transducer for installation at said contact surface, said transducer configured to produce a signal correlated to said moisture level at said contact surface for input to said fluid flow control circuit.

6. An apparatus according to claim 5 wherein said object is a door handle.

7. An apparatus according to claim 5 wherein said object is a push surface area of a door.

8. An apparatus according to claim 6 wherein said contact material is formed as a sleeve.

9. An apparatus according to claim 2 wherein said contact material is integrated within an object to provide said object with a continuously sanitized surface.

10. An apparatus according to claim 5 wherein said porous contact surface is nylon.

11. An apparatus according to claim 5 wherein said porous contact surface is a heat shrinkable fabric.

12. An apparatus according to claim 2 wherein said sanitizing fluid is scented.

13. A method for providing a contact surface which is continuously sanitized with a sanitizing fluid, said method comprising:
    (a) providing a reservoir containing said sanitizing fluid;
    (b) providing a contact material having a porous contact surface in fluid communication with said reservoir; and,
    (c) controlling the moisture level of said contact surface by producing a flow of said sanitizing fluid from said reservoir to said contact material when said moisture level has reached a predetermined level.

14. A method according to claim 13 whereby said sanitizing fluid is a chlorine-based, relatively non-flammable fluid.

15. A method according to claim 14 whereby said contact material comprises a durable, porous outer layer configured for evenly distributing said sanitizing fluid to said contact surface and a backing layer bonded to said outer layer to provide a seal there between.

16. A method according to claim 15 whereby said contact material covers the surface area of an object.

17. A method according to claim 16 whereby said object is a door handle.

18. A method according to claim 17 whereby said contact material is formed as a sleeve.

19. A method according to claim 13 whereby said contact material is integrated within an object to provide said object with a continuously sanitized surface.

* * * * *